US012050143B2

(12) United States Patent
Suresh

(10) Patent No.: US 12,050,143 B2
(45) Date of Patent: Jul. 30, 2024

(54) SYMMETRIC TRIMMING OF STRAIN GAUGES

(71) Applicant: Intuitive Surgical Operations, Inc., Sunnyvale, CA (US)

(72) Inventor: Ashwinram Suresh, San Jose, CA (US)

(73) Assignee: Intuitive Surgical Operations, Inc., Sunnyvale, CA (US)

( * ) Notice: Subject to any disclaimer, the term of this patent is extended or adjusted under 35 U.S.C. 154(b) by 245 days.

(21) Appl. No.: 17/761,054

(22) PCT Filed: Sep. 16, 2020

(86) PCT No.: PCT/US2020/051119
§ 371 (c)(1),
(2) Date: Mar. 16, 2022

(87) PCT Pub. No.: WO2021/055509
PCT Pub. Date: Mar. 25, 2021

(65) Prior Publication Data
US 2022/0341796 A1    Oct. 27, 2022

Related U.S. Application Data

(60) Provisional application No. 62/901,721, filed on Sep. 17, 2019.

(51) Int. Cl.
*G01L 1/22* (2006.01)
*H01C 10/23* (2006.01)

(52) U.S. Cl.
CPC .......... *G01L 1/2287* (2013.01); *G01L 1/2262* (2013.01); *H01C 10/23* (2013.01)

(58) Field of Classification Search
CPC ...... H01C 10/23; G01L 1/2287; G01L 1/2262
See application file for complete search history.

(56) References Cited

U.S. PATENT DOCUMENTS

| 4,034,778 A | 7/1977 | Sage et al. |
| 4,223,752 A | 9/1980 | Belcher |
| 4,329,878 A | 5/1982 | Utner et al. |
| 4,331,035 A | 5/1982 | Eisele et al. |
| 4,419,734 A | 12/1983 | Wolfson et al. |
| 4,428,976 A | 1/1984 | Eisele et al. |
| 4,456,293 A | 6/1984 | Panissidi |

(Continued)

FOREIGN PATENT DOCUMENTS

| CN | 202158916 U | 3/2012 |
| DE | 19523523 A1 | 1/1996 |

(Continued)

OTHER PUBLICATIONS

Office Action for CN Application No. 2020800784493, mailed Aug. 25, 2023, 11 pages.

(Continued)

*Primary Examiner* — Kyung S Lee

(57) ABSTRACT

A circuit is provided that includes a strain gauge resistor having a center axis and multiple conductor layer segments and a trim region extending along the center axis; wherein a first portion of the strain gauge resistor is located on one side of the center axis and a second portion of the strain gauge resistor is located on an opposite side of the center axis.

17 Claims, 7 Drawing Sheets

(56) References Cited

U.S. PATENT DOCUMENTS

| | | | |
|---|---|---|---|
| 4,522,072 A | 6/1985 | Sulouff et al. | |
| 4,657,097 A | 4/1987 | Griffen | |
| 4,777,826 A * | 10/1988 | Rud, Jr. | G01L 9/045 |
| | | | 338/195 |
| 4,787,256 A | 11/1988 | Cherbuy et al. | |
| 4,869,113 A | 9/1989 | Sarrazin | |
| 4,932,253 A | 6/1990 | McCoy | |
| 5,327,791 A | 7/1994 | Walker | |
| 5,723,826 A | 3/1998 | Kitagawa et al. | |
| 5,784,542 A | 7/1998 | Ohm et al. | |
| 5,855,583 A | 1/1999 | Wang et al. | |
| 6,197,017 B1 | 3/2001 | Brock et al. | |
| 6,331,181 B1 | 12/2001 | Tierney et al. | |
| 6,394,998 B1 | 5/2002 | Wallace et al. | |
| 6,459,926 B1 | 10/2002 | Nowlin et al. | |
| 6,494,882 B1 | 12/2002 | Lebouitz et al. | |
| 6,594,552 B1 | 7/2003 | Nowlin et al. | |
| 6,675,663 B1 | 1/2004 | Irion et al. | |
| 6,763,716 B2 | 7/2004 | Nagahara et al. | |
| 6,817,974 B2 | 11/2004 | Cooper et al. | |
| 6,910,392 B2 | 6/2005 | Lockery et al. | |
| 6,979,873 B2 | 12/2005 | Fujii | |
| 6,994,708 B2 | 2/2006 | Manzo | |
| 7,083,571 B2 | 8/2006 | Wang et al. | |
| 7,169,141 B2 | 1/2007 | Brock et al. | |
| 7,935,130 B2 | 5/2011 | Williams | |
| 8,444,631 B2 | 5/2013 | Yeung et al. | |
| 8,479,969 B2 | 7/2013 | Shelton, IV | |
| 8,506,555 B2 | 8/2013 | Ruiz Morales | |
| 8,551,115 B2 | 10/2013 | Steger et al. | |
| 8,602,288 B2 | 12/2013 | Shelton, IV et al. | |
| 8,620,473 B2 | 12/2013 | Diolaiti et al. | |
| 8,628,518 B2 | 1/2014 | Blumenkranz et al. | |
| 8,771,270 B2 | 7/2014 | Burbank | |
| 8,800,838 B2 | 8/2014 | Shelton, IV | |
| 9,028,494 B2 | 5/2015 | Shelton, IV et al. | |
| 9,101,734 B2 | 8/2015 | Selkee | |
| 9,204,923 B2 | 12/2015 | Manzo et al. | |
| 9,232,979 B2 | 1/2016 | Parihar et al. | |
| 9,707,684 B2 | 7/2017 | Ruiz et al. | |
| 9,782,214 B2 | 10/2017 | Houser et al. | |
| 9,952,107 B2 | 4/2018 | Blumenkranz et al. | |
| 10,085,809 B2 | 10/2018 | Blumenkranz et al. | |
| 10,622,125 B1 * | 4/2020 | Ogawa | H01C 1/14 |
| 2003/0150276 A1 | 8/2003 | Christensen et al. | |
| 2005/0050960 A1 | 3/2005 | Haines | |
| 2005/0139018 A1 * | 6/2005 | Haggstrom | G01L 1/26 |
| | | | 73/862.628 |
| 2006/0070464 A1 | 4/2006 | Walker | |
| 2007/0096666 A1 | 5/2007 | Ippisch | |
| 2009/0324161 A1 | 12/2009 | Prisco | |
| 2010/0024574 A1 | 2/2010 | Werthschutzky et al. | |
| 2010/0324453 A1 | 12/2010 | Lal et al. | |
| 2011/0071543 A1 | 3/2011 | Prisco et al. | |
| 2011/0282356 A1 | 11/2011 | Solomon et al. | |
| 2011/0283804 A1 | 11/2011 | Jost et al. | |
| 2012/0116391 A1 | 5/2012 | Houser et al. | |
| 2013/0291654 A1 | 11/2013 | Blumenkranz et al. | |
| 2014/0257333 A1 | 9/2014 | Blumenkranz | |
| 2015/0021105 A1 | 1/2015 | Head et al. | |
| 2015/0075250 A1 | 3/2015 | Kosa et al. | |
| 2015/0330856 A1 | 11/2015 | Chiou et al. | |
| 2015/0374447 A1 | 12/2015 | Blumenkranz et al. | |
| 2015/0374449 A1 | 12/2015 | Chowaniec et al. | |
| 2016/0146685 A1 | 5/2016 | Chiou et al. | |
| 2017/0261306 A1 | 9/2017 | Ausserlechner et al. | |
| 2018/0067003 A1 | 3/2018 | Michiwaki | |
| 2019/0069966 A1 | 3/2019 | Petersen et al. | |
| 2020/0129261 A1 | 4/2020 | Eschbach | |
| 2020/0278265 A1 | 9/2020 | Suresh | |

FOREIGN PATENT DOCUMENTS

| | | |
|---|---|---|
| EP | 0244324 B1 | 7/1989 |
| EP | 2644145 A1 | 10/2013 |
| ES | 2000423 A4 | 3/1998 |
| FR | 2598226 B1 | 4/1989 |
| GB | 2293453 B | 10/1996 |
| JP | H02223836 A | 9/1990 |
| JP | H0875572 A | 3/1996 |
| JP | H08201202 A | 8/1996 |
| KR | 970004983 A | 1/1997 |
| KR | 100703861 B1 | 4/2007 |
| WO | WO-2011163442 A1 | 12/2011 |
| WO | WO-2015120108 A1 | 8/2015 |
| WO | WO-2019099562 A1 | 5/2019 |
| WO | WO-2021055509 A2 | 3/2021 |

OTHER PUBLICATIONS

International Search Report and Written Opinion for Application No. PCT/US2020/051119, mailed Mar. 26, 2021, 16 pages.

Vertut. J, and Coiffet, P., "Robot Technology: Teleoperation and Robotics Evolution and Development," English translation, Prentice-Hall, Inc., Inglewood Cliffs, NJ, USA 1986, vol. 3A, 332 pages.

* cited by examiner

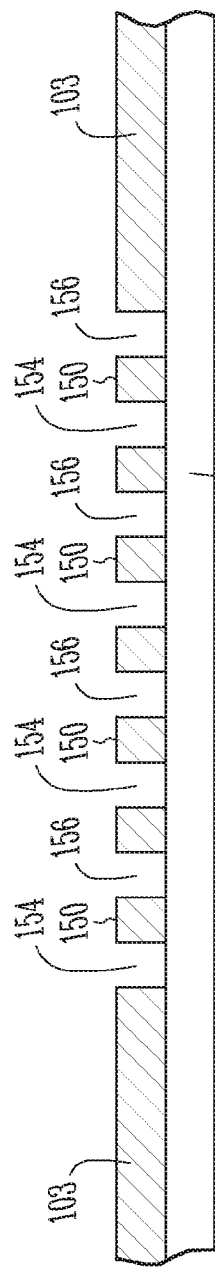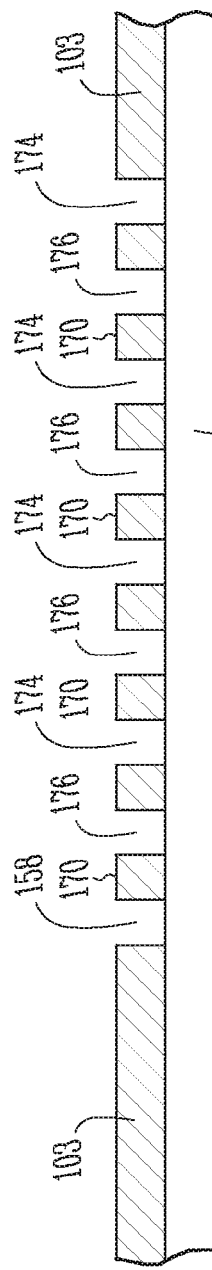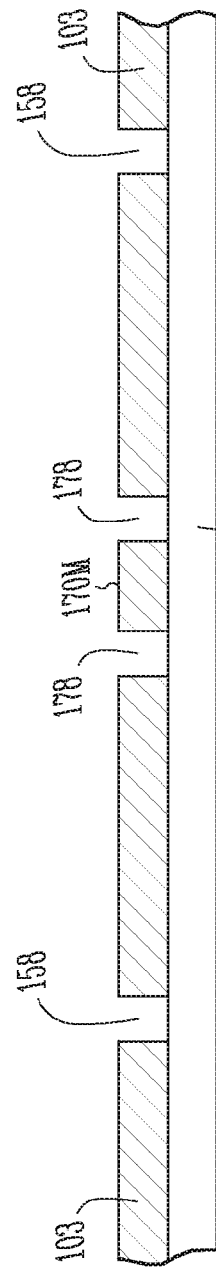

SYMMETRIC TRIMMING OF STRAIN GAUGES

CLAIM OF PRIORITY

This application is a U.S. national stage filing under 35 U.S.C. § 371 of International Application No. PCT/US2020/051119, entitled "SYMMETRIC TRIMMING OF STRAIN GAUGES," filed Sep. 16, 2020, which claims the benefit of priority to U.S. Provisional Patent Application Ser. No. 62/901,721, entitled "SYMMETRIC TRIMMING OF STRAIN GAUGES," filed on Sep. 17, 2019, each of the disclosures of which is incorporated by reference herein in its entirety.

BACKGROUND

Force sensing and feedback during a minimally invasive surgical procedure bring better immersion, realism and intuitiveness to a surgeon performing the procedure. For the best performance of haptics rendering and accuracy, force sensors may be placed on a surgical instrument and as close to the anatomical tissue interaction as possible. One approach to haptics accuracy is to use a force sensor that includes multiple electrical strain gauges, coupled in a Wheatstone bridge configuration, located on a beam at a distal end of a surgical instrument shaft. The strain gauges can be formed on the beam through printing or additive deposition processes, for example. The strain gauges also can be added through a printing process, for example. The force sensor measures changes in force imparted to the beam. A bridge circuit configuration is an electrical circuit topology in which two circuit branches (usually in parallel with each other) are bridged by a third branch connected between the first two branches at some intermediate point along them.

To have the ability to amplify an output signal from a bridge circuit, it often is desirable to have a DC offset of the bridge circuit close to zero when the bridge is in a nominal (e.g., no force imparted to the beam) condition. This generally requires that the bridge is balanced and the resistance of corresponding strain gauges in opposing halves of the bridge have matching resistance values. Often, the strain gauges are trimmed during their fabrication to achieve matching resistance values to balance the bridge.

For example, FIG. 1 is an illustrative top view of an example circuit 10 that includes a tension gauge strain gauge resistor 12 and compression strain gauge resistor 32 and trim regions 22, 42. The tension gauge strain resistor 12 includes a plurality of parallel first elongated segments 13 separated by first finger-like non-conducting regions 14 that alternately extend from first and second non-conducting boundary regions 16, 18. The tension gauge strain resistor 12 defines a first serpentine current flow path 20. Resistance of the tension gauge resistor 12 can be adjusted by adjusting the first current flow path 20 by trimming the length of a first non-conducting regions 14 used as trimming segment, such as the non-conducting region 14 within dashed lines 22. The compression gauge strain resistor 32 includes a plurality of vertically aligned second elongated segments 33 that are arranged perpendicular to the first segments 13 and that are separated by finger-like second non-conducting regions 34 that alternately extend from third and fourth non-conducting boundary regions 36, 38. The compression gauge strain resistor 32 defines a second serpentine current flow path 40. Resistance of the compression gauge resistor 32 can be adjusted by the second current flow path 40 by trimming the length of a second non-conducting region 34 used as a trimming segment, such as the non-conducting region 34 within dashed lines 42.

Previous approaches to trimming a strain gauge can result in undesirable variations of sensitivity to strain across strain gauge. Prior approaches to trimming to balance strain gauge resistances can result in an apparent shift in placement location of the strain gauges with respect to an initial intended placement location, which can introduce errors in force measurement that can be unacceptable in high precision force sensors.

SUMMARY

In one aspect, a force sensor is provided that includes a beam having a neutral axis, a tension strain gauge resistor and a compression strain gauge resistor that share a center axis aligned parallel to the neutral axis. The tension strain gauge resistor includes multiple first conductor segments arranged to provide a first current path and includes a first trim region that extends along the center axis. A first portion of the tension strain gauge resistor is located on one side of the center axis and a second portion of the tension strain gauge resistor is located on an opposite side of the center axis. The compression strain gauge resistor includes multiple second conductor segments arranged to provide a second current path and includes a second trim region that extends along the center axis. A first portion of the compression strain gauge resistor is located on one side of the center axis and a second portion of the compression strain gauge resistor is located on an opposite side of the center axis.

In another aspect, a compression gauge force sensor is provided that includes a beam having a neutral axis and a strain gauge resistor having a center axis arranged parallel to the neutral axis. The strain gauge sensor includes multiple conductor segments arranged to provide a first current path and includes a nonconducting trim region extending along the center axis. A first portion of the strain gauge resistor is located on one side of the center axis and a second portion of the strain gauge resistor is located on an opposite side of the center axis. One of the multiple conductor segments is arranged parallel to the center axis. The other conductor segments are arranged perpendicular to the center axis. The trim region bisects a portion of the one of the multiple conductor segments.

In another aspect, a method is provided to adjust resistance of a strain gauge circuit. The strain gauge resistor is trimmed along a center axis between a first portion of the strain gauge resistor having a first resistance and a first layout pattern and a second portion of the strain gauge resistor having a second resistance that matches the first resistance and having a second layout pattern that matches the first layout pattern.

BRIEF DESCRIPTION OF THE DRAWINGS

In the drawings, which are not necessarily drawn to scale, like numerals may describe similar components in different views. Like numerals having different letter suffixes may represent different instances of similar components. The drawings illustrate generally, by way of example, but not by way of limitation, various embodiments discussed in the present document.

FIG. 2B is an illustrative cross-section side view of a thin slice of the example T-resistor along line 2B-2B in FIG. 2A.

FIG. 2C is an illustrative cross-section side view of a thin slice of the example C-resistor along line 2C-2C in FIG. 2A.

FIG. 2D is an illustrative cross-section side view of a thin slice of the example C-resistor along line 2D-2D in FIG. 2A.

DETAILED DESCRIPTION

Figure 1:
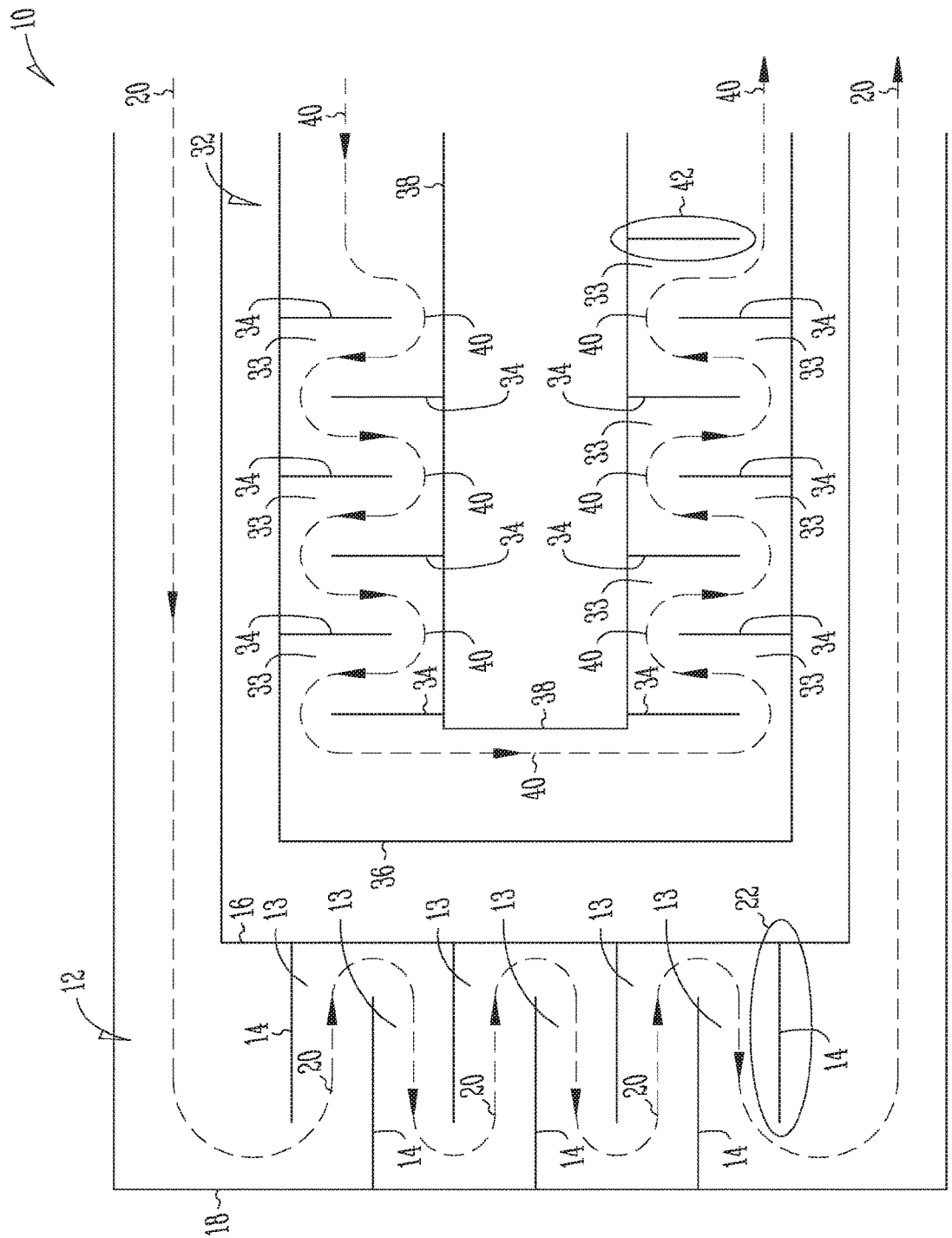
FIG. 1 is an illustrative top view of an example circuit that includes a tension gauge strain gauge resistor and compression strain gauge resistor and trimming segments.
Figure 2A:
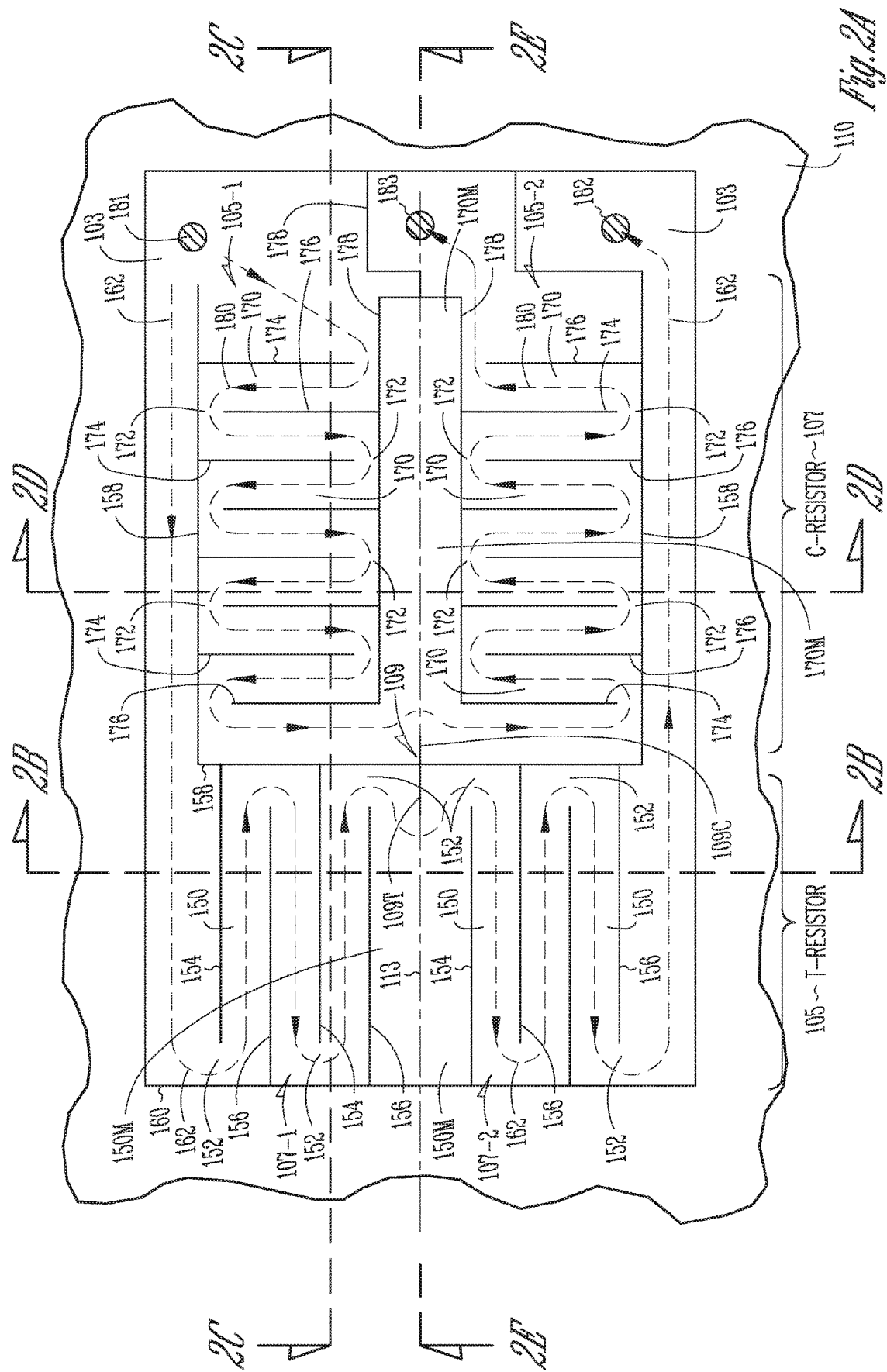
FIG. 2A is an illustrative top view an example circuit that includes a tension gauge strain gauge resistor and compression strain gauge resistor each having matching resistances and resistance patterns about a center axis and having a trim gap along the center axis.

FIG. 2A is an illustrative top view of an example tension gauge strain gauge resistor 105 and compression strain gauge resistor 107 each arranged to have matching resistances and resistance layout patterns on opposite sides of a center axis 113 and having a trimmed region 109 arranged along the center axis 113. More particularly, FIG. 2A shows an example force sensor 100 that includes a beam 106 having a side surface 110 with a tension gauge strain gauge resistor 105 and compression strain gauge resistor 107 thereon. A planar conductor region 103 located on the side surface 110 is contoured to include non-conducting regions 152, 154, 156, 160 that together, define the tension strain gauge resistor ('T-resistor') 105. The planar conductor region 103 is contoured to also include non-conducting regions 174, 176, 156, 178 that together, define the compression strain gauge resistor ('C-resistor') 107. The contours of the T-resistor 105 and the C-resistor 107 determine their respective resistances and strain sensitivities. The T-resistor 105 and the C-resistor 107 share a common center axis 113, which extends parallel to the beam's neutral axis (not shown). A beam's neutral axis typically is equidistant from the sides of the beam. at a An example planar region material can include a conductor material such as Nickel chromium alloy, Constantan alloy, Karma alloy, for example.

A dimension of a non-conducting trimmed region 109 located along the center axis 113 can be adjusted to adjust resistance of the T-resistor 105. More particularly, in an example T-resistor 105, a length of a non-conducting T-resistor trimmed region portion 109T arranged along the center axis within a center trim segment 150M of the T-resistor that can be adjusted to adjust resistance of the T-resistor 105. Similarly, a dimension of the non-conducting trim region 109 located along the center axis 113 can be adjusted to adjust resistance of the R-resistor 105. More particularly, a length of a non-conducting C-resistor trimmed region portion 109C along the center axis 113 within a middle conductor segment 170M of the C-resistor 107 can be trimmed to adjust resistance of the C-resistor 107.

The T-resistor 105 includes a plurality of elongated tension resistor conductor segments 150 that are arranged in parallel with one another and with the center axis 113 and that are interconnected at opposite ends of the elongated conductor segments 150 by short segments 152 that extend perpendicular to the center axis 113, to form a continuous serpentine or snake-like first current flow path 162 between a first node 181 and a second node 182. Alternating first and second elongated nonconducting tension resistor gap regions 154, 156 extend finger-like, parallel to the center axis 113, between adjacent elongated T-resistor segments 150. The first tension resistor non-conducting gap regions 154 extend finger-like parallel to the center axis 113 from a first non-conducting boundary region 158. The second tension resistor non-conducting gap regions 156 extend finger-like parallel to the center axis 113 from a second non-conducting boundary region 160. In an example force sensor, 100, the first non-conducting boundary region 158 includes a first non-conducting gap boundary region and the second non-conducting boundary region 160 includes an outer edge of the planar conductor region 103. T-resistor current follows the first current flow path indicated by dashed lines 162 along the elongated segments 150 and the short segments 152 within the T-resistor 105, between the respective first and second nodes 181, 182.

The short segments 152 are wider than the long segments so as to reduce the total of resistance of all the short segment 152 in comparison to total resistance of all the long segment 150. In an example tension strain gauge resistor 105 widths of the short segments 152 are at least three times and preferably at least four times widths of the first tension resistor conducting regions 150.

The example T-resistor 105 includes an odd number of elongated conductor segments 150. Specifically, the example T-resistor includes seven elongated segments 150. A middle elongated segment 150M arranged parallel to the center axis 113 is located between two groups of three elongated segments 150 also arranged parallel to the center axis 113. The center axis 113 bisects a portion of the middle elongated segment 150M. The non-conducting T-resistor trim region 109T extends from the first non-conducting boundary region 158 along the center axis into the middle elongated segment 150M. The length of the non-conducting T-resistor trim region 109T affects the first current flow path 162, which determines resistance of the T-resistor 105. The greater the length of the non-conducting T-resistor trim region 109T, the longer the first current flow path and the 162, and the larger the resistance value of the T-resistor 105.

The C-resistor 107 includes a plurality of elongated compression resistor conductor segments 170 that are arranged in parallel with one another and perpendicular to the center axis 113 and that are interconnected at opposite ends of the elongated conductor segments 170 by short segments 172 that extend parallel to the center axis 113, to form a continuous serpentine or snake-like second resistor path 180 between the first node 181 and a third node 183. Alternating first and second elongated nonconducting compression resistor gap regions 174, 176 extend finger-like, parallel to the center axis 113, between adjacent elongated C-resistor segments 170. The first compression resistor non-conducting gap regions 174 extend finger-like parallel to the center axis 113 from the first non-conducting boundary region 158. The second compression resistor non-conducting gap regions 176 extend finger-like parallel to the center axis 113 from a third non-conducting boundary region 178. In an example force sensor, 100, the third non-conducting boundary region 178 includes a non-conducting gap region. The second current flow path indicated by dashed lines 180 extends within the elongated segments 170 and the short segments 172 within the C-resistor 107, between the respective first and third nodes 181, 183.

The short segments 172 are wider than the long segments 170 so as to reduce the total of resistance of all the short segment 172 in comparison to total resistance of all the long segment 170. In an example compression strain gauge resistor 107 widths of the short segments 172 are at least three times and preferably at least four times widths of the four times the width of the second compression resistor conducting regions 170.

The example C-resistor 107 also includes an adjustable middle elongated conductor segment 170M arranged parallel to the center axis 113. The C-resistor 107 includes multiple elongated conductor segments 170 arranged peripheral to the middle conductor segment 170M and perpendicular to the center axis 113. Specifically, the example C-resistor 107 includes seventeen elongated conductor segments. The middle elongated middle conductor segment 170M is arranged parallel to the center axis 113 and is located between two groups of eight elongated peripheral segments 170 that are arranged about the middle conductor segment 170M and perpendicular to the center axis 113. The center axis 113 bisects a portion of the middle elongated trim segment 170M. The non-conducting C-resistor trim region 109C extends from the first non-conducting boundary region 158 along the center axis 113 into the middle elongated trim segment 170M of the C-resistor 107. The length of the non-conducting C-resistor trim region 109C affects the second current flow path 180, which determines resistance of the C-resistor 107. More particularly, the greater the length of the non-conducting C-resistor trim region 109C, the longer the second current flow path 180, and the larger the resistance value of the C-resistor 107.

The center axis bisects the T-resistor 105. The T-resistor includes a first T-resistor portion 105-1 located on one side of the center axis 113 and includes a second T-resistor portion 105-2 located on an opposite side of the center axis 113. Resistance values and resistance layout patterns match within the first and second T-resistor portions 105-1, 105-2. As used herein, the term 'resistance pattern' of a strain gauge resistor refers to the layout of the strain gauge resistor. In the example T-resistor 105, the first and second T-resistor portions 105-1, 105-2 are symmetrically arranged about the center axis 113. In the example T-resistor 105, three conductor segments 150 and one-half of the middle conductor segment 150M are included in the first T-resistor portion 105-1, and three conductor segments 150 and the other one-half of the middle conductor segment 150M are included in the second T-resistor portion 105-2. In the example T-resistor 105, the first and second T-resistor portions 105-1, 105-2 are mirror images of one another about the center axis 113.

Similarly, the center axis bisects the C-resistor 107. The C-resistor 107 includes a first C-resistor portion 107-1 located on one side of the center axis 113 and includes a second C-resistor portion 107-2 located on an opposite side of the center axis 113. Resistance and resistance patterns match within the first and second C-resistor portions 107-1, 107-2. In the example C-resistor 107, the first and second C-resistor portions 107-1, 107-2 are symmetrically arranged about the center axis 113. In the example C-resistor 107, eight conductor segments 170 and one-half of the middle conductor segment 170M are included in the first C-resistor portion 107-1, and eight conductor segments 170 and the other one-half of the middle conductor segment 170M are included in the second C-resistor portion 107-2. In the example C-resistor 107, the first and second C-resistor portions 107-1, 107-2 are mirror images of one another about the center axis 113.

The first and second T-resistor portions 105-1, 105-2 have matching sensitivity to strain since their resistance values and resistance patterns match. Likewise, the first and second C-resistor portions 107-1, 107-2 have matching sensitivity to strain since their resistance values and resistance patterns match. As used herein, the term, 'sensitivity to strain' refers to a relationship between change in strain due to force and corresponding change in resistance, when the force is applied along the sensing plane. As used herein, 'matching strain sensitivity' on opposite sides of a center axis 113 refers to a matching relationship between change in force and change in resistance at corresponding matching locations on opposites sides of the center axis.

During production and testing, a length dimension of the non-conducting T-resistor trim gap portion 109T along the center axis 113 can be adjusted to adjust resistance of the T-resistor 105. Since the length of the non-conducting T-resistor trim region 109T is adjusted along the center axis 113 and since the T-resistor is symmetrical about the center axis 113, adjusting the length of the trim region 109T does not upset the matching relationships between resistance, resistance patterns and sensitivity to strain of the first and second T-resistor portions 105-1, 105-2. Similarly, during production and testing, a length dimension of the non-conducting C-resistor trim region 109C along the center axis 113 can be adjusted to adjust resistance of the C-resistor 107. Since the length of the non-conducting C-resistor trim gap portion 109C is adjusted along the center axis 113 and since the C-resistor 107 is symmetrical about the center axis 113, adjusting the length of the trim gap portion 109C does not upset the matching relationships between resistance, resistance patterns and sensitivity to strain of the first and second C-resistor portions 107-1, 107-2.

FIG. 2B is an illustrative cross-section side view of a thin slice of the example T-resistor 105 along line 2B-2B in FIG. 2A. The planar conductor region 103 is disposed upon a dielectric layer 185 including a material such as glass and polyamide, for example. Alternating first and second elongated nonconducting tension resistor gap regions 154, 156 extend between adjacent elongated T-resistor segments 150.

FIG. 2C is an illustrative cross-section side view of a thin slice of the example C-resistor 107 along line 2C-2C in FIG. 2A. The planar conductor region 103 is disposed upon the dielectric layer 185. Alternating first and second elongated nonconducting compression resistor gap regions 174, 176 extend between adjacent elongated C-resistor segments 170. Elongated C-resistor segments 170 at one end of the cross-section view is located between the first non-conducting boundary region 158 and one of the second elongated nonconducting compression resistor gap regions 176.

FIG. 2D is an illustrative cross-section side view of a thin slice of the example C-resistor 107 along line 2D-2D in FIG. 2A. The planar conductor region 103 is disposed upon the dielectric layer 185. The C-resistor 107 is bounded by the first non-conducting boundary region 158 and the third non-conducting boundary region 178. The middle elongated trim segment 170M, which extends parallel to the center axis 113, is located between branches of the third non-conducting region 178.

Figure 2E:
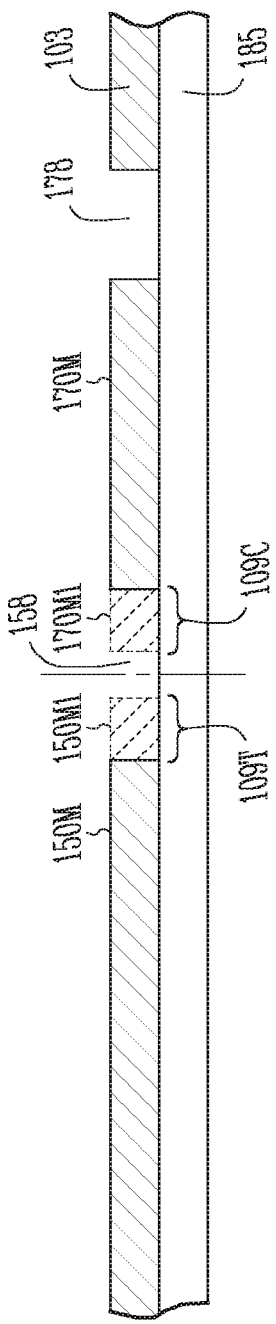
FIG. 2E is an illustrative cross-section side view of a thin slice of the example T-resistor and the example C-resistor along line 2E-2E in FIG. 2A showing example equal trimming within the middle trim segment of T-resistor and within the middle trim segment of the C-resistor.

FIG. 2E is an illustrative cross-section side view of a thin slice of the example T-resistor 105 and the example C-resistor 107 along line 2E-2E in FIG. 2A showing example equal trimming of the middle trim segment 150M of T-resistor 105 and the middle trim segment 170M of the C-resistor 107. The T-resistor trim region 109T and the C-resistor trim region 109C each intersect the first non-conducting boundary region 158. The respective dashed region 150M1 indicates a portion of the center portion 150M of the T-resistor 105 removed, through laser trimming or masking and chemical etching, for example, to adjust length of the T-resistor trim region 109T, to adjust resistance of the T-resistor 105. The respective dashed region 170M1 indicates a portion of the center portion 170M of the C-resistor 107 removed to adjust length of the C-resistor trim region 109C, to adjust resistance of the C-resistor 107. Equal amounts of the center portion 150M of the T-resistor 105 and of the center portion 170M of the C-resistor 107 are shown to have been removed in the example of FIG. 2E.

Figure 2F:
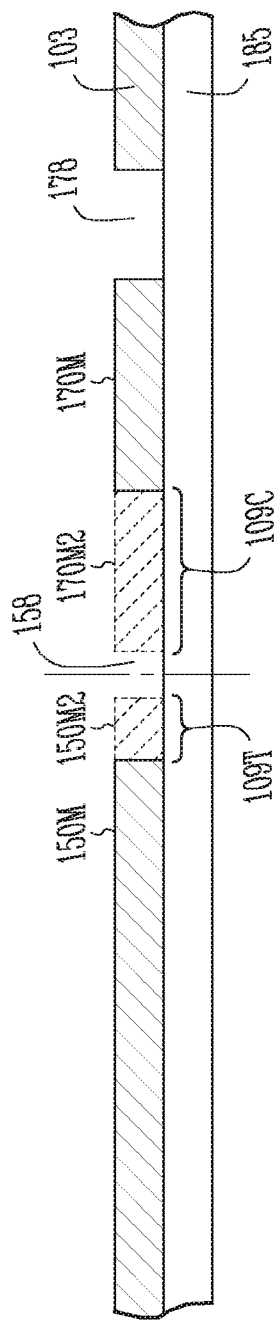
FIG. 2F is an illustrative cross-section side view of a thin slice of the example T-resistor and the example C-resistor along line 2E-2E in FIG. 2A showing example greater trimming within the middle trim segment of the C-resistor than within the middle trim segment of the T-resistor.

FIG. 2F is an illustrative cross-section side view of a thin slice of the example T-resistor 105 and the example C-resistor 107 along line 2E-2E in FIG. 2A showing example greater trimming within the middle trim segment 170M of the C-resistor 107 than within the middle trim segment 150M of the T-resistor 105. The respective dashed region 150M2 indicates a portion of the center portion 150M of the T-resistor 105 removed to adjust length of the T-resistor trim region 109T, to adjust resistance of the T-resistor 105. The respective dashed region 170M2 indicates a portion of the center portion 170M of the C-resistor 107 removed to adjust length of the C-resistor trim region 109C, to adjust resistance of the C-resistor 107.

Figure 2G:
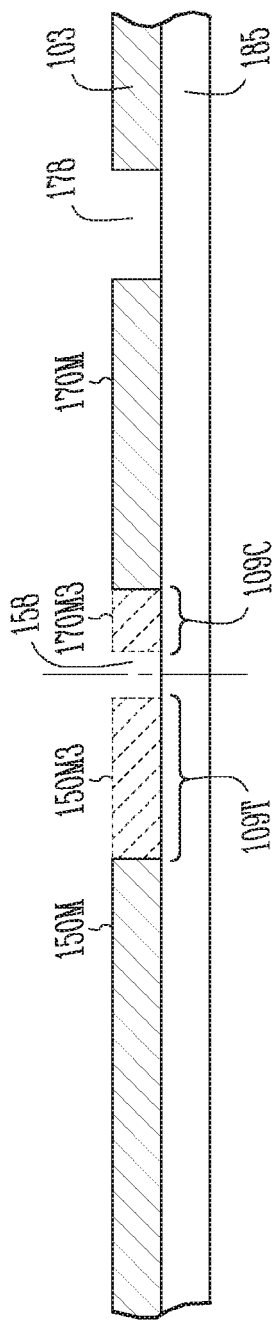
FIG. 2G is an illustrative cross-section view of a thin slice of the example T-resistor and the example C-resistor along line 2E-2E in FIG. 2A showing example greater trimming within the middle trim segment of the T-resistor than within the middle trim segments of the C-resistor.

FIG. 2G is an illustrative cross-section view of a thin slice of the example T-resistor 105 and the example C-resistor 107 along line 2E-2E in FIG. 2A showing example greater trimming within the middle trim segment 150M of the T-resistor 105 than within the middle trim segments 170M of the C-resistor 107. The respective dashed region 150M3 indicates a portion of the center portion 150M of the T-resistor 105 removed to adjust length of the T-resistor trim region 109T, to adjust resistance of the T-resistor 105. The respective dashed region 170M3 indicates a portion of the center portion 170M of the C-resistor 107 removed to adjust length of the C-resistor trim region 109C, to adjust resistance of the C-resistor 107.

Adjusting the length of the T-resistor trim region 109T adjusts the first current flow path 162. Increasing the length of the T-resistor trim region 109T increases current flow distance within the first current flow path 162. Increasing the length of the T-resistor trim region 109T increases current flow distance in a direction along the center axis 113 within the middle trim segment 150M. Similarly, adjusting the length of the C-resistor trim region 109C adjusts the second current flow path 180. Increasing the length of the C-resistor trim region 109C increases current flow distance within the second current flow path 180. Increasing the length of the C-resistor trim region 109C increases current flow distance in a direction along the center axis 113 within the middle trim segment 170M.

Figure 3:
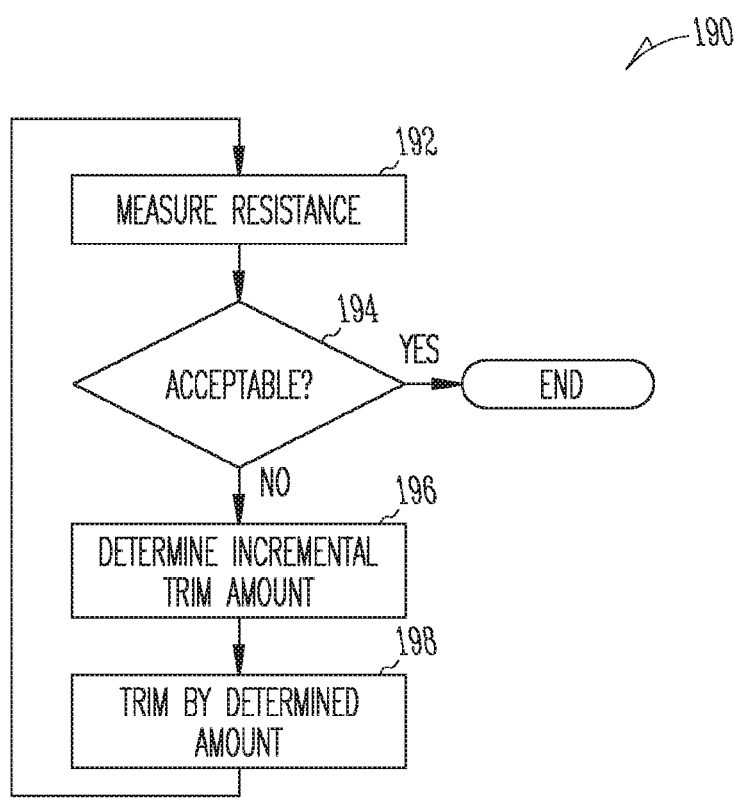
FIG. 3 is an illustrative flow diagram representing an example trim process.

FIG. 3 is an illustrative flow diagram representing an example trim process 190. An aim of the trim process, for example, can be to adjust resistance of a subject strain gauge resistor by incremental trimming i.e. removal, of conductor material. Alternatively, or in addition, an aim of the trim process, for example, can be to adjust or tune a zero offset of Wheatstone bridge to balance the bridge at a desired voltage when the bridge is powered. The incremental removal of conductor material incrementally increases resistance of the resistor. The process 190 can be used both for tension strain resistors and compression strain resistors. In step 192, resistance is measured across a subject strain gauge resistor. In decision step 194, a determine an is made as to whether the measured resistance is acceptable. In the case of producing and testing Wheatstone bridge circuit for example, an acceptable resistance can be one in which corresponding resistors within the bridge have matching resistance values. More particularly, for example, a typical bridge circuit is balanced in that resistance values of tension strain resistors match and resistance values of compression strain resistors match. If a measured resistance value is acceptable, then the process ends. If the measured resistance value is not acceptable, then at step 196, a trim amount is determined. In general, there is a known relationship between amount of conductor material removed and change in resistance. A trim amount is selected based upon a target resistance for a subject strain gauge resistor. In step 198, the subject resistor is trimmed by the determined amount. Trimming can involve using a laser to cut away a portion of the conductor region. Alternatively, for example, trimming can involve masking and chemical etching. The process then returns to step 192. Thus, the process 190 incrementally trims a subject strain gauge until a target resistance is reached. In the case of the T-resistor 105 of FIG. 2A, the process 190 involves incremental trimming to incrementally increase the length of the T-resistor trim region 109T, to incrementally increase the resistance of the T-resistor 105. In the case of the C-resistor 107 of FIG. 2A, the process 190 involves incremental trimming to incrementally increasing the length of the C-resistor trim region 109C to incrementally increase the resistance of the T-resistor 105.

Figure 4:
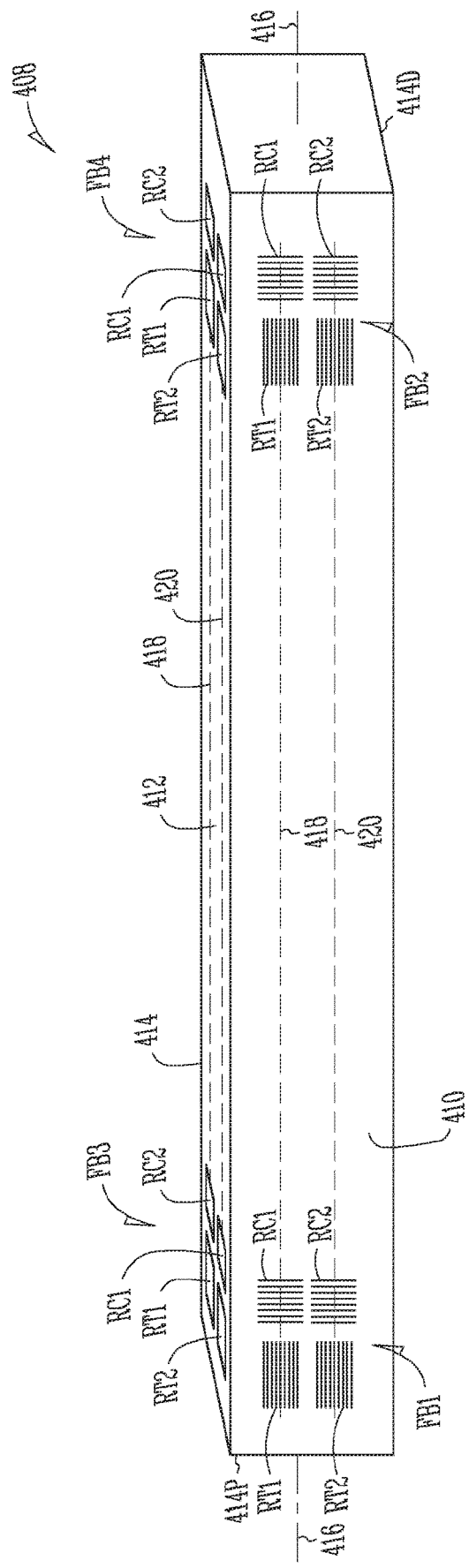
FIG. 4 is an illustrative perspective view of an example force sensor that includes a rectangular beam with four full-Wheatstone bridges (full-bridges).

FIG. 4 is an illustrative perspective view of an example force sensor 408 that includes a rectangular beam with four full-Wheatstone bridges (full-bridges) FB1-FB4. First and third full-bridge circuits FB1, FB3 are formed on a proximal end portion 414P of at respective orthogonal adjacent first and second faces 410, 412 of a rectangular beam 414. Second and fourth full-bridge circuits FB2, FB4 are formed on a distal end portion 414D of the at respective orthogonal adjacent first and second faces 410, 412 of the rectangular beam 414. Each bridge circuit includes first tension strain gauge $R_{T1}$ and a first compression strain gauge $R_{C1}$ and includes a second tension strain gauge $R_{T2}$ and a second compression strain gauge $R_{C2}$. The example strain gauge resistors $R_{T1}$ $R_{C1}$ $R_{T2}$ and $R_{C2}$ can include instances of the T-resistor 105 and C-resistor 107 of FIG. 2A and can be produced according to the process of FIG. 3. Each bridge circuit includes first strain gauge pair $R_{T1}/R_{C1}$ that includes a first tension strain gauge $R_{T1}$ and a first compression strain gauge $R_{C1}$ that are electrically coupled in series and includes a second strain gauge pair $R_{T2}/R_{C2}$ that includes a second tension strain gauge $R_{T2}$ and a second compression strain gauge $R_{C2}$ that are electrically coupled in series. The first strain gauge gauge pair $R_{T1}/R_{C1}$ of each bridge circuit is electrically coupled in parallel with a corresponding second tension strain gauge pair $R_{T2}/R_{C2}$ of the bridge circuit.

The respective first strain gauge pairs ($R_{T1}/R_{C1}$) of FB1 at the proximal end 414P and the distal end 414D are arranged upon the beam 414 along a first center axis 418 that extends along the first face 410 parallel to a beam neutral axis 416 that extends within the beam 414 equidistant from the sides of the beam 414. The respective second strain gauge pairs ($R_{T2}/R_{C2}$) of FB2 at the proximal end 414P and the distal end 414D are arranged upon the beam 414 along a second center axis 420 that extends along the first face 410 parallel to the beam neutral axis 416. The first pair ($R_{T1}/R_{C1}$) within the first bridge circuit FB1 at the proximal end portion of the beam 414 and first pair ($R_{T1}/R_{C1}$) within the second bridge circuit FB2 at the distal end portion of the beam 414 are arranged along and share a common first center axis 418. The second pair ($R_{T2}/R_{C2}$) within the first bridge circuit FB1 at the proximal end portion of the beam 414 and second pair ($R_{T2}/R_{C2}$) within the second bridge circuit FB2 at the distal end portion of the beam 114 are are arranged along and share a common second center axis 420. First and second strain gauge pairs of the third and fourth full bridges FB3, FB4 are similarly arranged along corresponding first and second center axes 418, 420 that extend along the second face 412 parallel to the neutral axis 416 through their respective first and second strain gauge pairs. While the description herein refers to a full bridge circuit, it will be appreciated that the strain gauge resistors described herein can be used in split full-bridge circuits and half-bridge circuits, for example, such as those described in U.S. Provisional Application Ser. 62/586,166, entitled. Force Sensor with Beam and Distributed Bridge Circuit, filed Nov. 17, 2017, which is expressly incorporated herein in its entirety by this reference.

Moreover, while the example force sensor 408 of FIG. 4 shows bridge circuits on two different side faces 410, 412, referred to herein as a 'two-sided' arrangement, an alternative example force sensor (not shown) can include bridge circuits on only one side face, referred to herein as a 'single-sided' arrangement. Alternative example double-sided and single sided arrangements can include full-bridge, split full-bridge circuits or half-bridge circuits.

Figure 5:
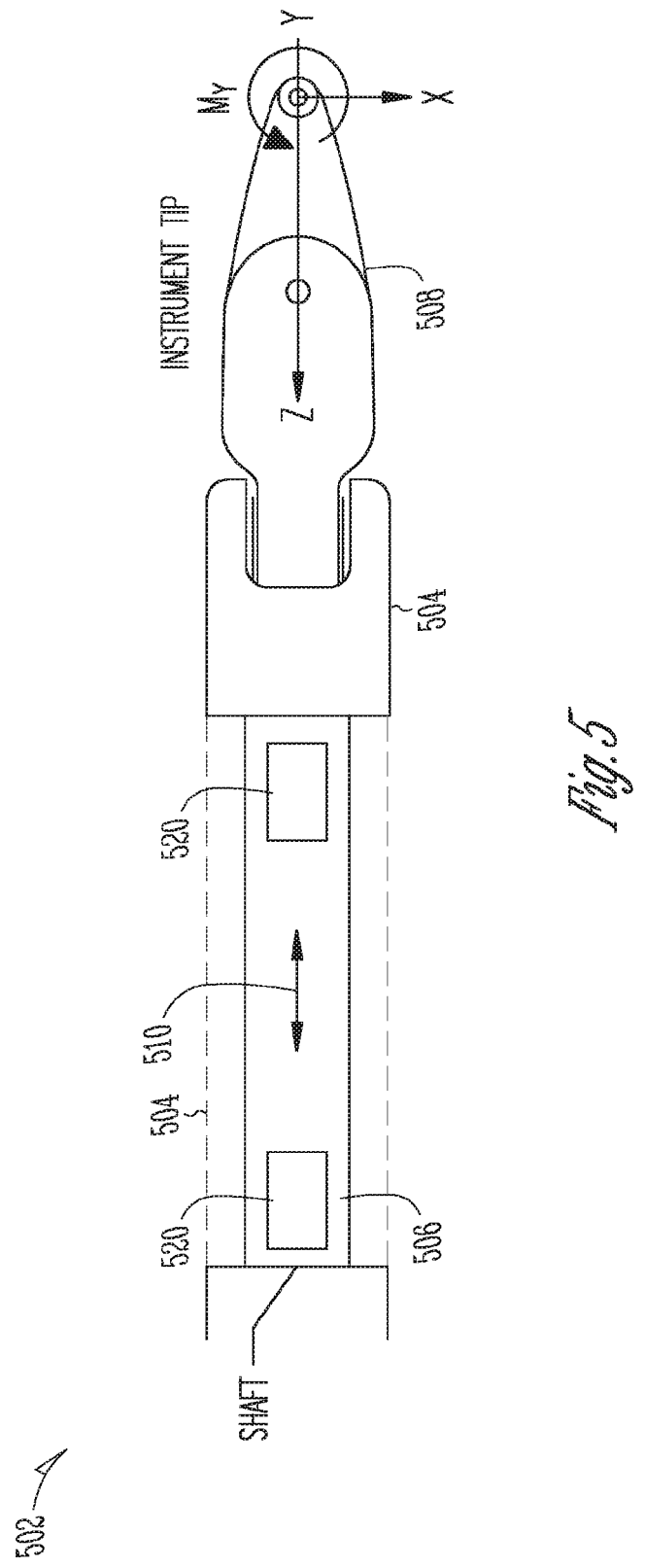
FIG. 5 is an illustrative side elevation view of a distal portion of a surgical instrument, shown in partially cut-way, having a force sensor beam mounted thereon, in accordance with some embodiments.

FIG. 5 is an illustrative side elevation view of a distal portion of a surgical instrument 502 with an elongated shaft 504, shown in partially cut-way, having a force sensor beam 206 mounted thereon, in accordance with some embodiments. The surgical instrument 502 includes an end effector 508, which may include articulatable jaws, for example. During a surgical procedure, the end effector 508 contacts anatomical tissue, which may result in X, Y. or Z direction forces and that may result in moment forces such as a moment $M_Y$ about a y-direction axis. The force sensor 506, which includes a longitudinal neutral axis 510, can be used to measure X and Y forces the longitudinal axis 510. The example beam 506 has a rectangular cross-section. A proximal full-bridge circuit 520 and a distal full-bridge circuit are located at opposite end portions of a side face of the beam 506. In another example beam, split full-bridge circuits or half-bridge circuits can be located upon a side face of the beam. Moreover, different alternate example beams can have double-sided arrangements of bridge circuits or single-sided arrangements of bridge circuits.

The above description is presented to enable any person skilled in the art to create and use symmetrically trimmed strain gauges. Various modifications to the examples will be readily apparent to those skilled in the art, and the generic principles defined herein may be applied to other examples and applications without departing from the scope of the invention. In the preceding description, numerous details are set forth for the purpose of explanation. However, one of ordinary skill in the art will realize that the examples in the disclosure might be practiced without the use of these specific details. In other instances, well-known processes are shown in block diagram form in order not to obscure the description of the invention with unnecessary detail. Identical reference numerals are used in some places to represent different views of the same or similar items in different drawings. Thus, the foregoing description and drawings of embodiments and examples are merely illustrative of the principles of the invention. Therefore, it will be understood that various modifications can be made to the embodiments by those skilled in the art without departing from the scope of the invention, which is defined in the appended claims.

The invention claimed is:

1. A force sensor comprising:
   a beam, a tension strain gauge resistor, and a compression strain gauge resistor;
   wherein the beam includes a neutral axis;
   wherein the tension strain gauge resistor is located on the beam and the compression strain gauge resistor is located on the beam;
   wherein the tension strain gauge resistor and the compression strain gauge resistor share a common center axis parallel to the neutral axis;
   wherein the tension strain gauge resistor includes multiple first conductor segments arranged to provide a first current path, a first nonconducting trim region extending along the center axis, a first portion of the tension strain gauge resistor located on a first side of the center axis, and a second portion of the tension strain gauge resistor located on a second side of the center axis opposite the first side of the center axis; and
   wherein the compression strain gauge resistor includes multiple second conductor segments arranged to provide a second current path, a second nonconducting trim region extending along the center axis, a first portion of the compression strain gauge resistor located on the first side of the center axis, and a second portion of the compression strain gauge resistor located on the second side of the center axis.

2. The force sensor of claim 1, wherein:
   a conductor segment of the first conductor segments is arranged parallel to the center axis, and the first nonconducting trim region bisects a portion of the conductor segment of the first conductor segments arranged parallel to the center axis;
   a conductor segment of the second conductor segments is arranged parallel to the center axis, and the second nonconducting trim region bisects a portion of the conductor segment of the second conductor segments arranged parallel to the center axis; and
   a conductor segment of the second conductor segments is arranged perpendicular to the center axis.

3. The force sensor of claim 1, wherein:
   a resistance of the first portion of the tension strain gauge resistor matches a resistance of the second portion of the tension strain gauge resistor; and
   a resistance of the first portion of the compression strain gauge resistor matches a resistance of the second portion of the compression strain gauge resistor.

4. The force sensor of claim 1, wherein:
   a resistance of the first portion of the tension strain gauge resistor matches a resistance of the second portion of the tension strain gauge resistor;
   a resistance of the first portion of the compression strain gauge resistor matches a resistance of the second portion of the compression strain gauge resistor;

a layout pattern of the first portion of the tension strain gauge resistor matches a layout pattern of the second portion of the tension strain gauge resistor; and a layout pattern of the first portion of the compression strain gauge resistor matches a layout pattern of the second portion of the compression strain gauge resistor.

5. The force sensor of claim 1, wherein:

the first portion of the tension strain gauge resistor is a mirror image of the second portion of the tension strain gauge resistor about the center axis; and the first portion of the compression strain gauge resistor is a mirror image of the second portion of the compression strain gauge resistor about the center axis.

6. The force sensor of claim 1, wherein:

the first nonconducting trim region of the tension strain gauge resistor bisects a portion of a middle elongated trim segment of the first conductor segments; and the second nonconducting trim region of the compression strain gauge resistor bisects a portion of a middle elongated trim segment of the second conductor segments.

7. The force sensor of claim 1, wherein:

the first conductor segments consist of an odd number of first conductor segments; and the first nonconducting trim region bisects a portion of a middle elongated trim segment of the first conductor segments.

8. The force sensor of claim 1, wherein:

the first conductor segments include a middle elongated trim segment located between an even number of other first conductor segments of the first conductor segments; and the nonconducting trim region bisects a portion of the middle elongated trim segment.

9. The force sensor of claim 1, wherein:

the first conductor segments are arranged to provide a serpentine first current path; and the second conductor segments are arranged to provide a serpentine second current path.

10. The force sensor of claim 1, wherein:

the force sensor includes multiple first nonconducting regions and multiple second nonconducting regions;

the first nonconducting regions include first nonconducting gaps between each of the first conductor segments, and the first nonconducting gaps are arranged to define the first conductor segments;

the second nonconducting regions include second nonconducting gaps between each of the second conductor segments, and the second nonconducting gaps are arranged to define the second conductor segments; and the first and second nonconducting regions are symmetrically arranged about the center axis.

11. The force sensor of claim 1, wherein:

a conductor segment of the first conductor segments is arranged parallel to the center axis;

multiple conductor segments of the second conductor segments are arranged parallel to the center axis and include a middle elongated trim segment;

a conductor segment of the second conductor segments is arranged perpendicular to the center axis;

the first nonconducting trim region bisects a portion of one of the first conductor segments; and the second nonconducting trim region bisects a portion of the middle elongated trim segment of the second conductor segments.

12. The force sensor of claim 1, wherein:

the force sensor includes a first node, a second node, and a third node;

the first conductor segments are arranged to provide a first current path between the first node and the second node; and the second conductor segments are arranged to provide a second current path between the first node and the third node.

13. A force sensor comprising:

a beam and a first strain gauge resistor;

wherein the beam has a neutral axis;

wherein the first strain gauge resistor is located on the beam and has a center axis parallel to the neutral axis of the beam;

wherein the first strain gauge resistor includes a first portion of the first strain gauge resistor located on a first side of the center axis, a second portion of the first strain gauge resistor located on a second side of the center axis opposite the first side, multiple conductor segments arranged to provide a first current path through the first portion and the second portion, and a nonconducting trim region extending along the center axis;

wherein the multiple conductor segments include a middle elongated trim segment arranged parallel to the center axis and other conductor segments arranged perpendicular to the center axis; and wherein the nonconducting trim region extends within a portion of the middle elongated trim segment.

14. The force sensor of claim 13, wherein:

a resistance of the first current path in the first portion of the first strain gauge resistor matches a resistance of the first current path in the second portion of the first strain gauge resistor; and a layout pattern of the first portion of the first strain gauge resistor matches a layout pattern of the second portion of the first strain gauge resistor.

15. The force sensor of claim 13, wherein:

an even number of the other conductor segments are on each side of the middle elongated trim segment.

16. The force sensor of claim 13, wherein:

the force sensor includes a first node, a second node, and a second strain gauge resistor;

the first current path is a serpentine current path defined by the multiple conductor segments between the first node and the second node; and the second strain gauge resistor is coupled to the second node.

17. The force sensor of claim 13, wherein:

the force sensor includes multiple nonconducting regions that include gaps between the multiple conductor segments; and the gaps are arranged to define the multiple conductor segments.

* * * * *